(12) United States Patent
Spencer et al.

(10) Patent No.: US 12,257,003 B2
(45) Date of Patent: Mar. 25, 2025

(54) OCCLUSION-CROSSING DEVICES, ATHERECTOMY DEVICES, AND IMAGING

(71) Applicant: Avinger, Inc.

(72) Inventors: Maegan K. Spencer, Emerald Hills, CA (US); John B. Simpson, Woodside, CA (US); Stephen C. Davies, El Dorado Hills, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 17/449,895

(22) Filed: Oct. 4, 2021

(65) Prior Publication Data

US 2022/0125525 A1    Apr. 28, 2022

Related U.S. Application Data

(63) Continuation of application No. 15/162,353, filed on May 23, 2016, now Pat. No. 11,135,019, which is a
(Continued)

(51) Int. Cl.
*A61B 34/20*    (2016.01)
*A61B 5/00*    (2006.01)
(Continued)

(52) U.S. Cl.
CPC ............ *A61B 34/20* (2016.02); *A61B 5/0062* (2013.01); *A61B 5/0066* (2013.01); *A61B 5/0084* (2013.01); *A61B 5/02007* (2013.01); *A61B 5/6852* (2013.01); *A61B 17/00234* (2013.01); *A61B 17/320725* (2013.01); *A61B 17/320758* (2013.01); *A61B 90/37* (2016.02); *A61B 6/12* (2013.01); *A61B 6/487* (2013.01); *A61B 2017/00296* (2013.01); *A61B 2017/22068* (2013.01); *A61B 2034/2055* (2016.02); *A61B 2034/2065* (2016.02);
(Continued)

(58) Field of Classification Search
CPC ......... A61B 8/12; A61B 8/0891; A61B 34/20; A61B 5/0066; A61B 5/0084; A61B 17/320758; G06T 7/0012; G06T 2207/10101; G06T 2207/30101
See application file for complete search history.

(56) References Cited

U.S. PATENT DOCUMENTS

| 3,367,727 A | 2/1968 | Ward et al. |
| 3,908,637 A | 9/1975 | Doroshow |

(Continued)

FOREIGN PATENT DOCUMENTS

| CN | 1875242 A | 12/2006 |
| CN | 1947652 A | 4/2007 |

(Continued)

OTHER PUBLICATIONS

Patel et al.; U.S. Appl. No. 17/455,655 entitled "Atherectomy catheter with shapeable distal tip," filed Nov. 18, 2021.
(Continued)

*Primary Examiner* — Jason M Ip
(74) *Attorney, Agent, or Firm* — Shay Glenn LLP

(57) ABSTRACT

Described herein are methods for producing and identifying characteristic ("crescent shaped") regions indicative of an atherectomy plaque within a vessel, and systems and devices adapted to take advantage of this characteristic region.

20 Claims, 6 Drawing Sheets

Related U.S. Application Data continuation of application No. 13/675,867, filed on Nov. 13, 2012, now Pat. No. 9,345,406, which is a continuation-in-part of application No. 13/433,049, filed on Mar. 28, 2012, now Pat. No. 8,644,913.

(60) Provisional application No. 61/559,013, filed on Nov. 11, 2011.

(51) Int. Cl.
| | |
|---|---|
| A61B 5/02 | (2006.01) |
| A61B 17/00 | (2006.01) |
| A61B 17/3207 | (2006.01) |
| A61B 90/00 | (2016.01) |
| A61B 6/00 | (2006.01) |
| A61B 6/12 | (2006.01) |
| A61B 17/22 | (2006.01) |
| A61B 90/30 | (2016.01) |

(52) U.S. Cl.
CPC . *A61B 2090/306* (2016.02); *A61B 2090/3614* (2016.02); *A61B 2090/3735* (2016.02); *A61B 90/39* (2016.02); *A61B 2217/007* (2013.01); *A61B 2562/0233* (2013.01)

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,002,560 A | 3/1991 | Machold et al. |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,449,372 A | 9/1995 | Schmaltz et al. |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,613,981 A | 3/1997 | Boyle et al. |
| 5,620,426 A | 4/1997 | Braithwaite |
| 5,632,754 A | 5/1997 | Farley et al. |
| 5,632,755 A | 5/1997 | Nordgren et al. |
| 5,667,490 A | 9/1997 | Keith et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,935,139 A | 8/1999 | Bates |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |

(56) References Cited

U.S. PATENT DOCUMENTS

| | | |
|---|---|---|
| 6,451,009 B1 | 9/2002 | Dasilva et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,673,042 B1 | 1/2004 | Samson et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,776,062 B2 | 8/2010 | Besselink et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,244,934 B2 | 4/2019 | Tachibana et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,406,316 B2 | 9/2019 | Garvey et al. |
| 10,470,795 B2 | 11/2019 | Patel et al. |
| 10,547,478 B2 | 1/2020 | Jang et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,860,484 B2 | 10/2020 | Simpson et al. |
| 10,869,685 B2 | 12/2020 | Patel et al. |
| 10,932,670 B2 | 3/2021 | Smith et al. |
| 10,952,615 B2 | 3/2021 | Kankaria |
| 10,952,763 B2 | 3/2021 | Newhauser et al. |
| 11,033,190 B2 | 6/2021 | Patel et al. |

(56) References Cited

U.S. PATENT DOCUMENTS

| | | |
|---|---|---|
| 11,076,773 B2 | 8/2021 | Patel et al. |
| 11,096,717 B2 | 8/2021 | Gupta et al. |
| 11,134,849 B2 | 10/2021 | Simpson et al. |
| 11,135,019 B2 | 10/2021 | Spencer et al. |
| 11,147,583 B2 | 10/2021 | Patel et al. |
| 11,206,975 B2 | 12/2021 | Tachibana et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0114875 A1 | 6/2003 | Sjostrom |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0163085 A1 | 8/2003 | Tanner et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0021075 A1 | 1/2005 | Bonnette et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soto et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |

(56) References Cited

U.S. PATENT DOCUMENTS

| | | |
|---|---|---|
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0073455 A1 | 3/2009 | Onimura |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0137140 A1 | 6/2011 | Tearney et al. |
| 2011/0144673 A1 | 6/2011 | Zhang et al. |
| 2011/0201924 A1 | 8/2011 | Teamney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Teamey et al. |
| 2012/0123352 A1 | 5/2012 | Fruland et al. |
| 2012/0136350 A1 | 5/2012 | Goshgarian et al. |
| 2012/0238869 A1 | 9/2012 | Schmitt et al. |
| 2012/0259337 A1 | 10/2012 | del Rio et al. |
| 2012/0277730 A1 | 11/2012 | Salahleh et al. |
| 2012/0289971 A1 | 11/2012 | Segermark et al. |
| 2013/0023865 A1 | 1/2013 | Steinke et al. |
| 2013/0035692 A1 | 2/2013 | Sorensen et al. |
| 2013/0072787 A1 | 3/2013 | Wallace et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0222042 A1 | 8/2014 | Kessler et al. |
| 2014/0371718 A1 | 12/2014 | Alvarez et al. |
| 2015/0025310 A1 | 1/2015 | Everingham et al. |
| 2015/0141816 A1 | 5/2015 | Gupta et al. |
| 2015/0320975 A1 | 11/2015 | Simpson et al. |
| 2016/0144155 A1 | 5/2016 | Simpson et al. |
| 2018/0207417 A1 | 7/2018 | Zung et al. |
| 2019/0021679 A1 | 1/2019 | Christensen |
| 2019/0029714 A1 | 1/2019 | Patel et al. |
| 2019/0110809 A1 | 4/2019 | Rosenthal et al. |
| 2019/0209206 A1 | 7/2019 | Patel et al. |
| 2019/0313941 A1 | 10/2019 | Radjabi |
| 2020/0060718 A1 | 2/2020 | Patel et al. |
| 2020/0069253 A1 | 3/2020 | Black et al. |
| 2020/0315654 A1 | 10/2020 | Patel et al. |
| 2020/0323553 A1 | 10/2020 | Fernandez et al. |
| 2021/0059713 A1 | 3/2021 | Patel et al. |
| 2021/0076949 A1 | 3/2021 | Smith et al. |
| 2021/0177262 A1 | 6/2021 | Spencer et al. |
| 2021/0267621 A1 | 9/2021 | Simpson et al. |
| 2021/0330345 A1 | 10/2021 | Newhauser et al. |
| 2021/0345903 A1 | 11/2021 | Patel et al. |
| 2022/0168011 A1 | 6/2022 | Patel et al. |
| 2022/0273336 A1 | 9/2022 | Fernandez et al. |
| 2022/0273337 A1 | 9/2022 | Patel et al. |

FOREIGN PATENT DOCUMENTS

| | | |
|---|---|---|
| CN | 101601581 A | 12/2009 |
| CN | 103027727 A | 4/2013 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | H05501065 A | 3/1993 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |

(56) References Cited

FOREIGN PATENT DOCUMENTS

| | | |
|---|---|---|
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2008/151155 A2 | 12/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |

OTHER PUBLICATIONS

Aziz et al.; Chronic total occlusions—a stiff challenge requiring a major breakthrough: is there light at the end of the tunnel ?; Heart; vol. 91; suppl. III; pp. 42-48; Jun. 2005.

Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vemelle.noel/Plastic_Snap_fit_design.pdf) on Sep. 26, 2018.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Leitgeb et al.; Performance of fourier domain vs time domain optical coherence tomography; Optics Express; 11(8); pp. 889-894; Apr. 21, 2003.

Linares et al.; Arbitrary single-mode coupling by tapered and nontapered grin fiber lenses; Applied Optics; vol. 29; No. 28; pp. 4003-4007; Oct. 1, 1990.

Merriam Webster; Proximal (Definition); 10 pages; retrieved from the internet (https://www.merriam-webster.com/dictionary/proximal) on Jun. 9, 2021.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical experiences; Cardiovascular and Interventional Radiology; Springer-Verlag; 22(6); pp. 504-509; Nov. 1, 1999.

Sharma et al.; Common-path optical coherence tomography with side-viewing bare fiber probe for endoscopic optical coherence tomography; Rev. Sci. Instrum.; vol. 78; 113102; 5 pages; Nov. 6, 2007.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Stamper et al.; Plaque characterization with optical coherence tomography. Journal of the American College of Cardiology. 47(8); pp. 69-79; Apr. 18, 2006.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Wikipedia; Hinge; 4 pages; retrieved from the internet (https://en.wikipedia.org/w/index.php?title=Hinge&oldid=479569345) on Jun. 9, 2021.

Smith et al.; U.S. Appl. No. 17/189,123 entitled "Optical pressure sensor assembly," filed Mar. 1, 2021.

Kankaria; U.S. Appl. No. 17/209,162 entitled "Optical coherence tomography with graded index fiber for biological imaging," filed Mar. 22, 2021.

Patel et al.; U.S. Appl. No. 17/347,419 entitled "Micro-molded anamorphic reflector lens for image guided therapeutic/diagnostic catheters," filed Jun. 14, 2021.

Gupta et al.; U.S. Appl. No. 17/445,648 entitled "Tissue collection device for catheter," filed Aug. 23, 2021.

Simpson et al.; U.S. Appl. No. 17/449,867 entitled "Occlusion-crossing devices, imaging, and atherectomy devices," filed Oct. 4, 2021.

Patel et al.; U.S. Appl. No. 17/450,658 entitled "High speed chronic total occlusion crossing devices," filed Oct. 12, 2021.

Tachibana et al.; U.S. Appl. No. 17/645,722 entitled "Atherectomy catheter drive assemblies," filed Dec. 22, 2021.

Black et al.; U.S. Appl. No. 17/652,073 entitled "Optical coherence tomography for biological imaging," filed Feb. 22, 2022.

Patel et al.; U.S. Appl. No. 17/762,815 entitled "Atherectomy catheter with shapeable distal tip," filed Mar. 23, 2022.

(56) References Cited

OTHER PUBLICATIONS

Patel et al.; U.S. Appl. No. 17/763,810 entitled "Occlusion-crossing devices," filed Mar. 25, 2022.
Patel et al.; U.S. Appl. No. 17/816,673 entitled "Atherectomy catheter with serrated cutter," filed Aug. 1, 2022.

OCCLUSION-CROSSING DEVICES, ATHERECTOMY DEVICES, AND IMAGING

CROSS REFERENCE TO RELATED APPLICATIONS

This application is a continuation of U.S. patent application Ser. No. 15/162,353, filed on May 23, 2016, titled "OCCLUSION-CROSSING DEVICES, ATHERECTOMY DEVICES, AND IMAGING," now U.S. Pat. No. 11,135,019, which is a continuation of U.S. patent application Ser. No. 13/675,867, filed Nov. 13, 2012, titled "OCCLUSION-CROSSING DEVICES, ATHERECTOMY DEVICES, AND IMAGING," now U.S. Pat. No. 9,345,406, which claims the benefit under 35 U.S.C. 119 of U.S. Provisional Patent Application No. 61/559,013, filed Nov. 11, 2011, titled "ATHERECTOMY METHODS AND DEVICES." U.S. patent application Ser. No. 13/675,867 also a continuation-in-part of U.S. patent application Ser. No. 13/433,049, filed Mar. 28, 2012, titled "OCCLUSION-CROSSING DEVICES, IMAGING, AND ATHERECTOMY DEVICES," now U.S. Pat. No. 8,644,913. Each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, methods and systems described herein are related to the treatment, identification, and removal of atheroma. In particular, described herein are systems, methods, devices and techniques for identifying distinguishing morphology in vessel images to direct or orient interventional devices.

BACKGROUND

Coronary artery disease is the leading cause of death within the United States for men and women. It is characterized by a buildup of material (often fatty) in the internal lumen of the coronary arteries. It is also associated with the hardening of the arterial walls. The buildup of material commonly starts on one side of the vessel and grows across the open lumen. As such, the last point of patency often occurs at the boundary between the material deposit (disease) and the healthy vessel.

Atherectomy is the process of removing diseased tissue from a stenosed lumen so as to restore patency and blood flow. There currently exist a number of devices that facilitate atherectomy. However, the operation of such devices has a number of shortcomings. In some instances, the active element of the atherectomy device acts equally in all directions, requiring the device to reside in the center of the diseased portion to maintain optimum efficacy. In other instances, the active element is directional but as such needs some method of visualization to orient the active element with respect to the diseased tissue. In many instances, the method of visualization that is employed is angiography, which is only capable of giving a silhouette of the open lumen.

Further, minimally invasive techniques for treating coronary artery disease, such as atherectomy, typically involve the placement of a guidewire through the occlusion prior to performing the atherectomy. For example, a chronic total occlusion (CTO) device can be used to place a guidewire through the occlusion and ultimately cross through the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

Moreover, minimally invasive surgical procedures to treat coronary artery disease depend on the precise positioning and manipulation of interventional devices. Guidance provided by high-resolution imaging can enable the characterization of tissue and lesion properties in vivo prior to treatment. As the majority of atherogenesis occurs in an eccentric fashion within the artery, therapeutic tools that have onboard imaging provide a distinct opportunity to selectively treat the diseased portion of a vessel. Even with on-board imaging techniques, however, it can be difficult to interpret the images so as to properly orient and steer the interventional devices as needed.

Accordingly, there is a need for a consistent and precise mechanism for steering or orienting occlusion-crossing, atherectomy, or other interventional devices. The invention described herein is based on the novel realization that a characteristic morphology (or morphological structure) may be visualized when (or after) passing a structure through the lumen of a vessel containing an atherectomy plaque mass (atheroma).

SUMMARY OF THE DISCLOSURE

The present invention relates to methods of forming and/or identifying characteristic morphologies within a vessel that indicate the presence, orientation and location of plaque masses within the vessel. Also described are devices to image, identify, and use this characteristic morphology (e.g., morphological structure) to orient a device, and/or remove or navigate the plaque in the peripheral or coronary vasculature.

In general, in one embodiment, a method of identifying an atherectomy plaque mass in a vessel includes applying circumferential radial force within the vessel to displace a rigid plaque mass and force the vessel wall to stretch away from the device; imaging the vessel to create an image; and identifying crescent-shaped structures associated with an atherectomy plaque in the image.

This and other embodiments can include one or more of the following features. The method can further include identifying the orientation of a plaque mass based on the directionality of the crescent-shaped structures. The method can further include identifying the position of a plaque mass relative to outer layered structures of a vessel wall based on the crescent-shaped structures. Imaging the vessel can include imaging the vessel with optical coherence tomography. The method can further include inserting a device into the vessel, and the device can apply the circumferential radial force. Imaging the vessel can include imaging with an imaging sensor attached to the device. The method can further include orienting the device within the vessel based on the crescent-shaped structures. Orienting the device can include pointing a directional cutter at a plaque mass identified based upon the crescent-shaped structure. Orienting the device can include directing the device based upon the relationship between markers in the image and the crescent-shaped structures. The method can further include rotating the imaging sensor to obtain the image.

In general, in another embodiment, a method of identifying an atherectomy plaque mass within a vessel includes the steps of: applying circumferential radial force within the vessel to displace a rigid plaque mass and forcing the vessel wall to stretch away from the device; visualizing the vessel wall following the application of circumferential radial force; and identifying crescent-shaped structures. The crescent-shaped structures may be formed by the application of circumferential radial force from within the lumen of the vessel.

This and other embodiments may include one or more of the following features. The method may also include the step of identifying the orientation of a plaque mass based on the directionality of the crescent-shaped structures. In some variations, the method may also include the step of identifying the position of a plaque mass relative to the outer layered structures of a vessel based on the crescent-shaped structures. In some variations, the method may also include the step of orienting a device or therapeutic tool within the vessel based on the crescent-shaped structures.

Any of the methods described herein can be carried out by a controller. Thus, an imaging system can be configured to detect, label, and/or highlight the characteristic morphological structures and/or use them to automatically detect or suggest the location of an atheroma.

In general, in one embodiment, an atherectomy device includes a distal end configured to dissect plaque from within a vessel. The device includes an elongate catheter body, a troweled distal tip extending from the catheter body and a rotatable cutter. The troweled distal tip has a curved outer surface configured to conform to an outer vessel and a scooped inner edge configured to at least partially plane along the plaque. The rotatable cutter is at least partially within the troweled distal tip.

This and other embodiments can include one or more of the following features. The device can further include an OCT sensor near or on the rotatable cylindrical cutter and configured to image radially into the vessel. The device can further include an inner lumen opening through the rotatable cutter into which material cut by the device may be driven. The rotatable cutter can be partially covered by the curved outer surface and can be partially exposed proximate to the scooped inner edge. The device can be configured to self-orient within the vessel.

In general, in another embodiment, an atherectomy device includes a distal end configured to dissect an atherectomy plaque using visual cues generated by a device with on-board optical coherence tomography, the device comprising: an elongate catheter body; a distal tip having a shaped opening (which may be a beveled opening, a trowel-shaped opening, or a tongue-shaped opening); a rotatable cylindrical cutter at least partially within the troweled or tongue-shaped opening; an OCT sensor near or on the rotatable cylindrical cutter and configured to image around the periphery of the catheter and into the vessel; and an inner lumen open through the rotatable cutter into which atherectomy material may be driven.

This and other embodiments can include one or more of the following features. The device may include a rotatable drive shaft for rotating the cutting element (cylindrical cutter) and/or the OCT sensor. Other elements may also or alternatively be included. In some variations, the distal tip is generally trowel or shovel-shaped in order to match the morphology of the plaque/wall interface revealed by the characteristic crescent shape described herein.

DETAILED DESCRIPTION

When crossing an occlusion of a blood vessel and imaging the vessel, such as with optical coherence tomography (OCT), an unexpected, yet predictable and characteristic morphology (or geometry) can be identified. The resulting characteristic morphology, described further herein, is formed at the boundary between the layered vessel wall structures and a plaque mass when crossing a chronic total occlusion (CTO) with a catheter or crossing device such as those described in: U.S. patent application Ser. No. 12/689,748, filed Jan. 19, 2010, titled "GUIDEWIRE POSITIONING CATHETER," now Publication No. US-2010-0274270-A1; U.S. patent application Ser. No. 12/108,433, filed Apr. 23, 2008, titled "CATHETER SYSTEM AND METHOD FOR BORING THROUGH BLOCKED VASCULAR PASSAGES," now U.S. Pat. No. 8,062,316; U.S. patent application Ser. No. 12/829,277, filed Jul. 1, 2010, titled "ATHERECTOMY CATHETER WITH LATERALLY-DISPLACEABLE TIP," now Publication No. US-2011-0004107-A1; U.S. patent application Ser. No. 12/829,267, filed Jul. 1, 2010, titled "CATHETER-BASED OFF-AXIS OPTICAL COHERENCE TOMOGRAPHY IMAGING SYSTEM," now Publication No. US-2010-0021926-A1; U.S. patent application Ser. No. 12/790,703, filed May 28, 2010, titled "OPTICAL COHERENCE TOMOGRAPHY FOR BIOLOGICAL IMAGING," now Publication No. US-2010-0305452-A1; U.S. patent application Ser. No. 13/175,232, filed Jul. 1, 2011, titled "ATHERECTOMY CATHETERS WITH LONGITUDINALLY DISPLACEABLE DRIVE SHAFTS," now Publication No. US-2012-0046679-A1; U.S. patent application Ser. No. 13/433,049, filed Mar. 28, 2012, titled "OCCLUSION-CROSSING DEVICES, IMAGING, AND ATHERECTOMY DEVICES," now Publication No. US-2012-0253186-A1, each of which is herein incorporated by reference in its entirety. The characteristic morphology may formed as a result of a dissection plane that is generated between a plaque mass and the lumen walls while traversing a vascular lesion, e.g., in peripheral and coronary CTO intervention.

As described herein, the resulting morphology is highly characteristic and can be used to obtain information with respect to the position of the disease within and with respect to the vessel. This information can also be utilized in real-time to orient the therapeutic portion of a device (e.g., atherectomy cutter or pre-shaped tip, etc.) toward disease and away from healthy tissue.

Using an imaging modality, such as optical coherence tomography (OCT), it is possible to visualize the shape or geometry that is created when advancing a device through a vascular lesion, such as a CTO. In some instances, the distinguishing shape or morphology that results when passing through a vascular lesion is a crescent-shaped feature (or a pair of such features) which may be formed around the circumference of the device, as shown in FIGS. 1-3.

Figure 1:
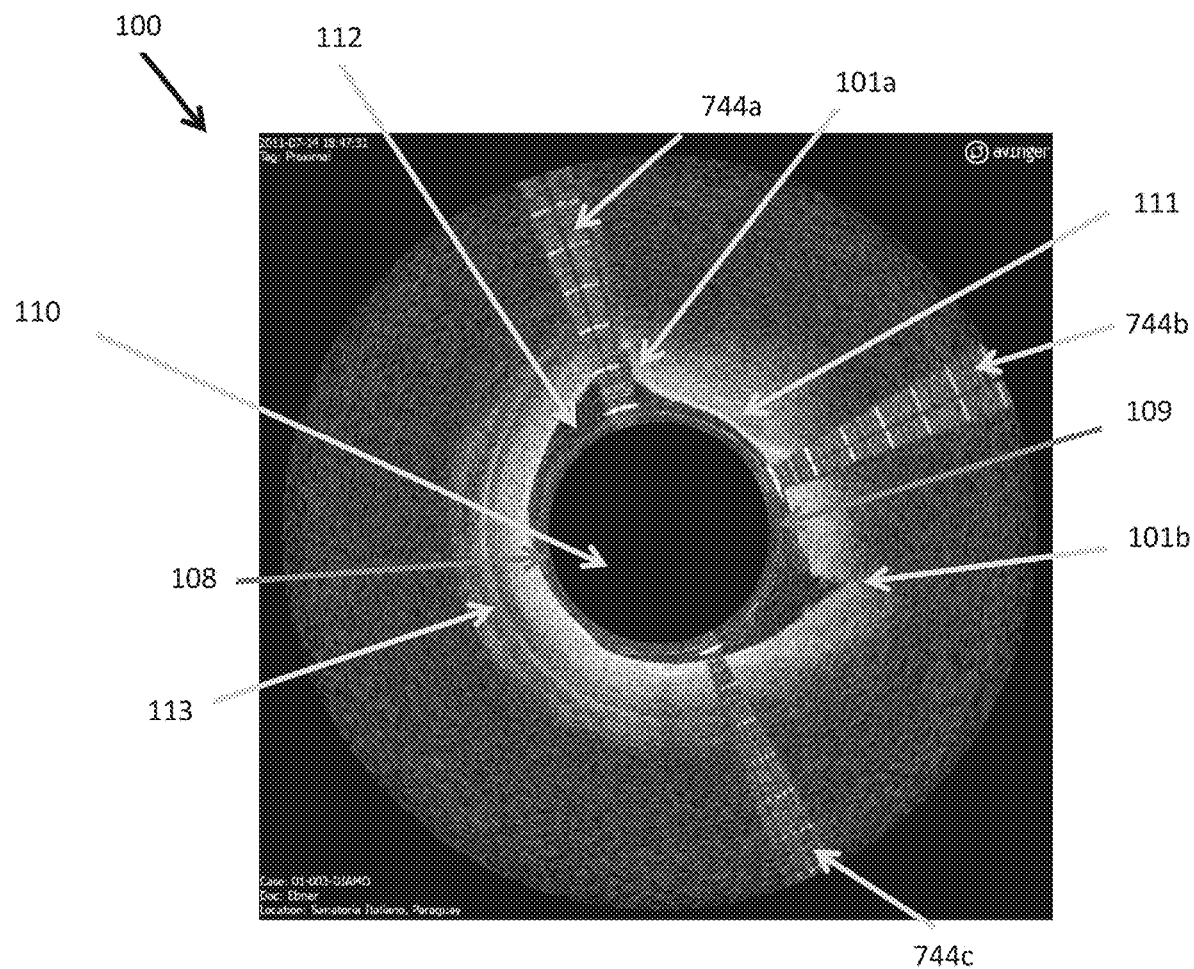
FIGS. 1-3 show examples of OCT images from within the lumen of a blood vessel, illustrating the crescent-shaped morphology described herein.
Figure 2:
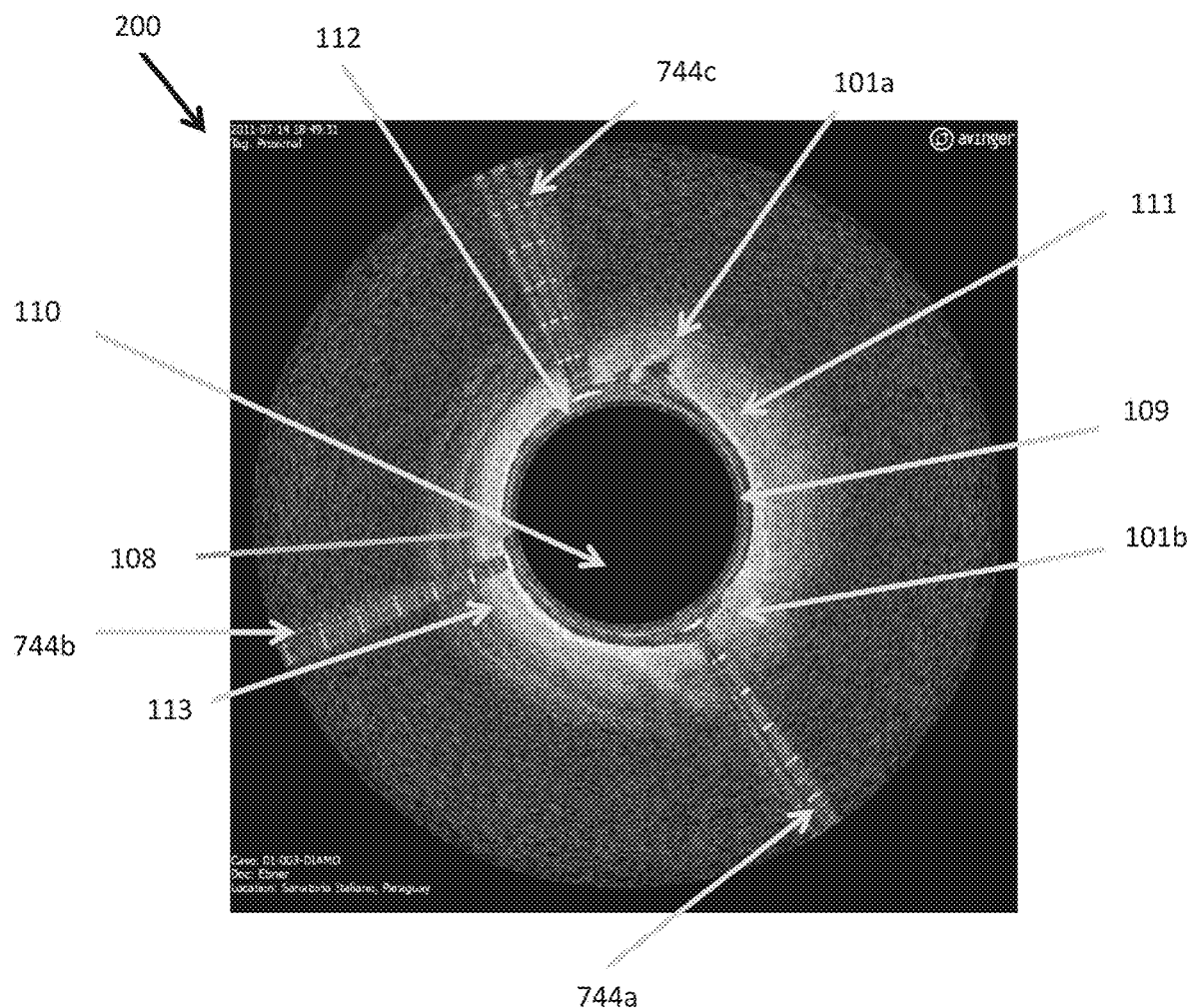
Figure 3:
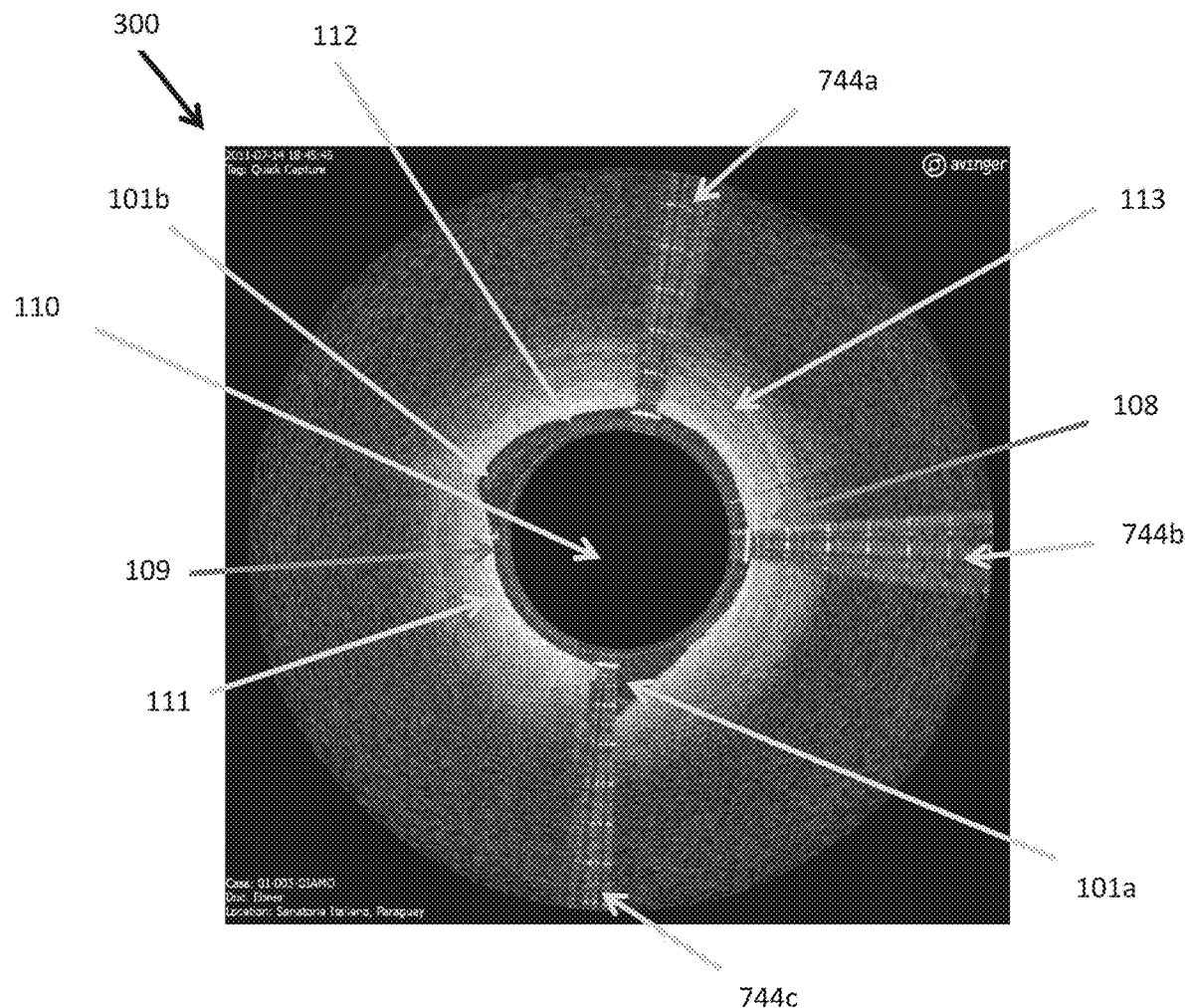

In FIGS. 1-3, the images are gathered by an occlusion-crossing catheter having a rotatable distal tip which allows the tip to be driven past the occluded region. The images in FIGS. 1-3 are generated by rotating an OCT imaging sensor around the lumen of the vessel. The tip of the catheter may be rotated both (or either) clockwise or counterclockwise. The rate of rotation may be constant or variable, and may be between about 1 and about 5000 rpms. The OCT imaging sensor may be located on the catheter (e.g., at or near the distal end), and the sensor may be rotated to enable circumferential imaging of the lumen (by rotating an end portion of the catheter, for example). The catheter may be held in a relatively fixed position within the lumen of the vessel or it may be moved longitudinally through the lumen while obtaining the images.

For example, FIG. 1 shows an OCT image taken from a catheter equipped to take OCT images from within a lumen of a vessel that is at least partially occluded. In this example, a catheter (which may include the OCT imaging catheter) has been inserted past the occluded region shown. In FIG. 1, the tip of the catheter has already passed through this occluded region of the vessel, and OCT image 100 was taken of the vessel after passage of the tip.

The image 100 shown includes a black circle 110, which is representative of the device itself. Around the black circle 110 extends a dark portion 112. The dark portion 112 forms a semi-circular-like shape (or a "D" shape) with a rounded portion 108 on one side and a substantially linear portion 109 on the other side (note that the substantially linear portion is shorter than the rounded portion 108 and can be slightly bowed in the opposite direction). The rounded portion 108 and the substantially linear portion 109 meet in characteristic crescents or "crescent wings" 101a, 101b (in this image 100 at the 11 and 4 o'clock positions, respectively) to give a "cat ear" shaped profile. The crescent wings 101a, 101b point inwards (towards the substantially linear portion 109) to frame an amorphous structure 111 indicating a plaque mass in the vessel. In contrast, the rounded portion 108 lies against layered structures 113 of different contrast, indicating healthy tissue of the vessel (e.g., intima, adventitia, media).

Although the inventions described herein are not bound by any particular theory, the characteristic morphology of bracketing crescents ("cat ears") shown and described with respect to FIG. 1 may be primarily due to the tendency for a device inserted within the vessel to track along the side of a plaque mass (between the plaque mass and the vessel wall) rather than through the plaque mass. As the device tracks along the side of the plaque mass, the wall of the vessel stays intact and stretches, thereby bowing out in a substantially circumferential manner along with the device (forming the rounded portion 108). In contrast, the plaque mass may undergo little, if any, stretching, thereby maintaining a substantially straight profile (forming the substantially linear portion 109). The dark portion 112 may be formed as blood is cleared by flushing through a lumen on the device or peripheral apparatus. The pointed portion of the crescent wings 101a, 101b may form as a result of the healthy tissue stretching around the cylindrically-shaped device, which is positioned between the plaque mass and the vessel outer wall (e.g., adventitia). Further, the black circle 110 is a feature that is added (e.g., by software) into the image to indicate the approximate shape and location of the device relative to the environment; the OCT sensor in this example does not image within the device itself.

Thus, the characteristic morphology described with respect to FIG. 1 may be mainly due to the tendency for a device placed within a clogged vessel to track along the side of a plaque mass. The morphology along this path may promote anisotropic stretching around the device. When circumferential radial forces are applied in this space, the rigid plaque mass is less likely to accommodate the introduced device, forcing the more compliant vessel wall to preferentially stretch away from the device. When visualized with onboard imaging, this morphology appears as crescent-shaped edges, with wings (crescent edges) that occur on each side of a plaque region. These wings (also referred to as crescents or cat ears) are typically bowed in one direction, forming a half-moon shape, as shown in FIG. 1. The directionality of these wings may be indicative of the position of a plaque mass relative to the outer layered structures of a vessel, e.g., the smaller side of the shape may be on the side of the plaque region. This shape is consistent with predications based on the relative compliance of vessel wall structures and disease.

Additional representative OCT images 200, 300 are also shown in FIGS. 2 and 3. Each image 200, 300 includes the same or similar characteristic morphology as described with respect to FIG. 1. The images 100, 200, and 300 all show the morphology in a slightly different orientation (for example, the crescent wings 101a, 101b are in the 11 o'clock and 4 o'clock positions in image 100 and the crescent wings 101a, 101b in the 6 o'clock and 10 o'clock positions in the FIG. 300). The second crescent shape in FIG. 2 101b is partially hidden behind the reference structure 744a. This difference in orientation between the images is a result of the varying nature of disease within a vessel and is dependent on the path that a CTO-crossing device takes while traversing through a lesion. This orientation may actively change while traversing a device through a diseased segment of a vessel.

The characteristic morphology shown in FIGS. 1-3 can be used as a marker to provide a real-time roadmap during an interventional procedure in diseased vasculature to aid in device placement. That is, the crescent-shaped characteristic features, with a plaque mass on one side and layered wall structures on the other, can be used as a clear guide during interventional procedures in the peripheral or coronary vasculature.

Further, the tip of an atherectomy and/or imaging device (including, for example, the cutting element or occlusion-crossing element) can be repositioned toward a plaque mass using the crescent morphology as a guide, enabling a device to track along the true lumen of a CTO and avoid perforation of the vessel. A therapeutic tool may also be positioned using this feature to remove or modify a plaque mass and avoid the outer wall structures of a vessel, preventing vessel perforation.

In one embodiment, marker features (e.g., fiducial markers) on the device can assist in aligning the device in the desired orientation relative to the crescent morphology. The markers can be configured to obstruct imaging from the OCT sensor at least once per rotation of the rotatable tip. For example, the markers on the device can be a radiopaque material (e.g., a metal) that can be seen in high contrast during fluoroscopy or a material that reflects or absorbs optical beams from the OCT system (e.g., metal, dense polymer, carbon powder). As described in more detail below, the imaging system may also be configured to identify, mark, and/or highlight these characteristic crescent morphological shapes and to display them as real-time markers. Other markers may also be shown by the imaging system, including makers displayed on the image that indicate the radial orientation of the device, structures in the tissue, etc. For example, markers may be overlaid on the image to achieve a similar result to physical markers on the catheter (e.g., electrically, magnetically, or in software). In some variations, a marker can be aligned with a distinguishing feature of the inserted device (e.g., catheter), such as a fixed jog or exposed cutter, to aid in steering or cutting with the device.

Figure 5:
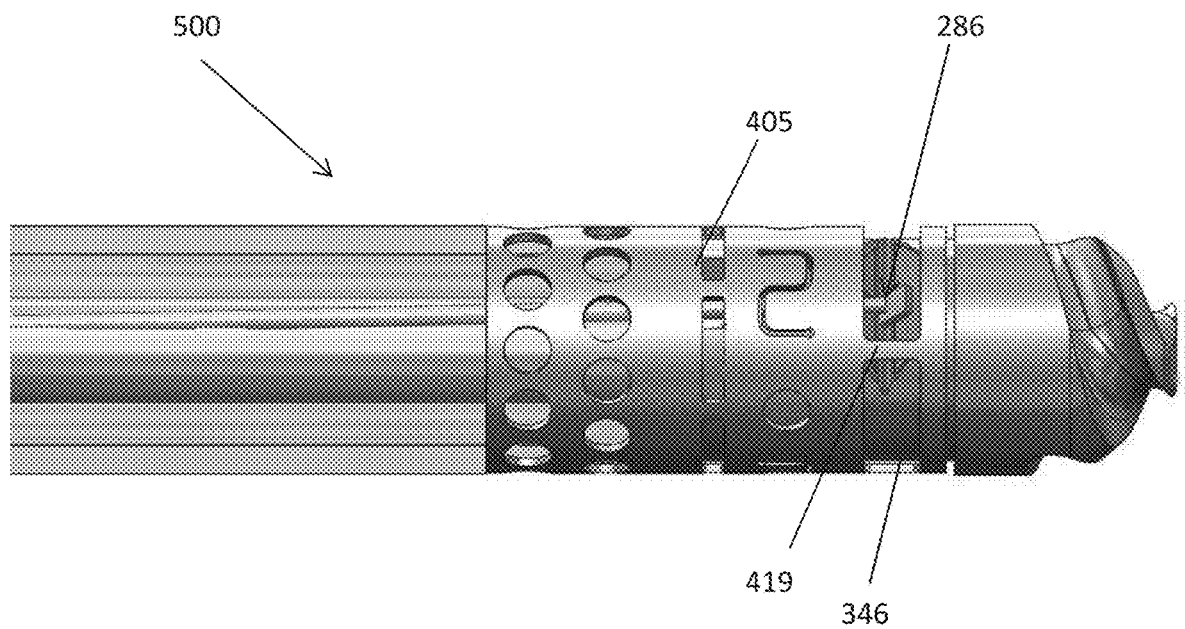
FIGS. 5 and 6 illustrate an exemplary device with markers configured to display on an OCT image.
Figure 6:
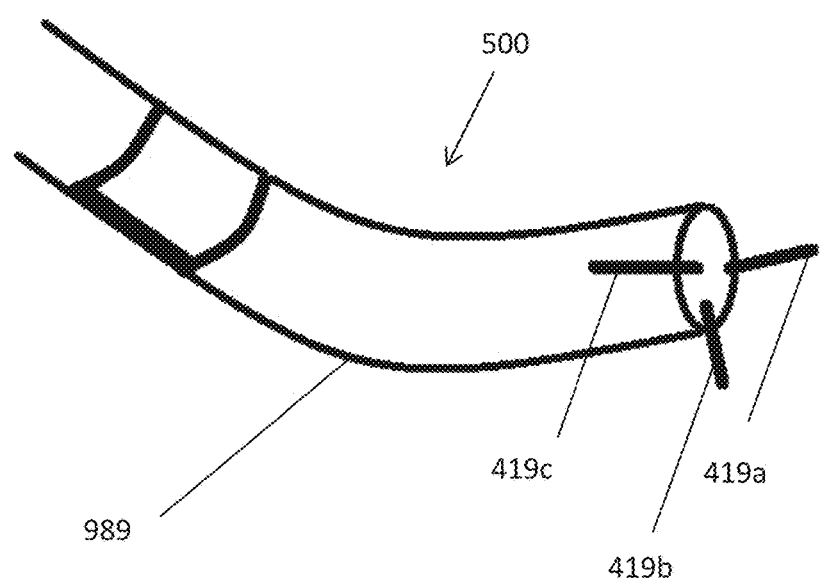

For example, as shown in FIG. 5, an occlusion-crossing device 500 can include a chassis 405 having three window regions 346 separated by spines 419 (which may be referred to as posts, struts, dividers, separators, etc.) arranged annularly around the chassis 405. These spines 419 may serve as reference markers as the imaging sensor 286 rotates and views the tissue through the windows 346. For example, spines may produce reference regions 744a, 744b, and 744c such as those shown in FIGS. 1-3. In some embodiments, as shown in FIG. 6, the spines 419 can be aligned relative to a jog 989 in the device (here such that the middle spine 419b is aligned opposite to the jog direction 989). This relative orientation can assist in pointing the jog and thus the end of the device in the desired direction.

The markers can thus produce corresponding reference regions in the images. Thus, in FIGS. 1-3, reference regions 744a, 744b, 744c in the form of striped rays indicate the locations of the markers or spines 419a, 419b, 419c, respectively, on the device 500. The reference regions 744a, 744b, 744c can thus indicate the orientation of the distal end of the catheter within the body.

During a CTO procedure, one goal may be to steer the catheter towards the plaque or unhealthy tissue. Because the middle spine 419b is aligned opposite to the jog 989 (as shown in FIG. 6), the ray 744b corresponding to the middle spine 419b can be oriented opposite to the non-healthy tissue or plaque 111 (indicated by the substantially linear portion 109 between the crescent wings 101a, 101b) to steer the catheter in the correct direction. FIG. 1 shows the catheter deflected toward the layered, healthy tissue. FIG. 2 shows the catheter rotated such that it is deflected toward the unhealthy, non-layered structure.

Thus, the system may be configured to allow the orientation of the catheter to be rotated into the correct position using fixed directional markers and the characteristic crescent wing morphology of the OCT images. It is to be understood that, although the images 100, 200, 300 are described as resulting from using a device similar to the occlusion-crossing device 500 that other device designs can be steered using the same morphology (for example, devices having different reference markers).

The crescent morphology described here can also provide direct, real-time feedback during an interventional procedure for general device repositioning based on the thickness of the layered wall structures, helping prevent perforation of the vessel. For example, the crescent morphology may indicate a plaque, however if the nearby layered wall structures appear to be very thin and perivascular structures can be seen in the OCT images beyond the layered structures, it is possible that the vessel is close to being perforated. In this case, the OCT image may serve as a warning sign, and the physician may pull the device proximal to reposition for a different approach.

An imaging system, and particularly an OCT imaging system as described, may be configured to detect, label, and/or highlight the crescent-shaped morphological structures in an image, and/or use them to automatically detect or suggest the location of an atheroma. For example, an imaging system may include a controller configured to automatically identify the crescent-shaped morphology within the OCT images. In some variations, this analysis is done separately from the imaging system (e.g., either concurrent or in real-time, or later, including as a post-procedure analysis). Likewise, in some embodiments, a controller can be configured to orient or steer a device through the vessel based upon images showing the characteristic crescent-shaped morphology. Standard image-processing algorithms may be used or adapted for use to identify the characteristic pair of crescents, which typically occur from the lumen of the vessel, radiating outward into the vessel wall. An imaging and/or image-processing system may execute (e.g., as executable code, firmware, software, hardware, etc.) image analysis logic that can determine if the crescent-shaped morphological structures are present in an image and/or indicate that they are present on the image. For example, analysis logic may determine if the structures are present in an OCT image, and may also identify them in any appropriate manner, e.g., by marking, etc. Likewise, the imaging and/or image-processing system may execute image analysis logic that can determine the direction in which the crescent-shaped structures point and, thus, the location of an atheroma therebetween.

Figure 7:
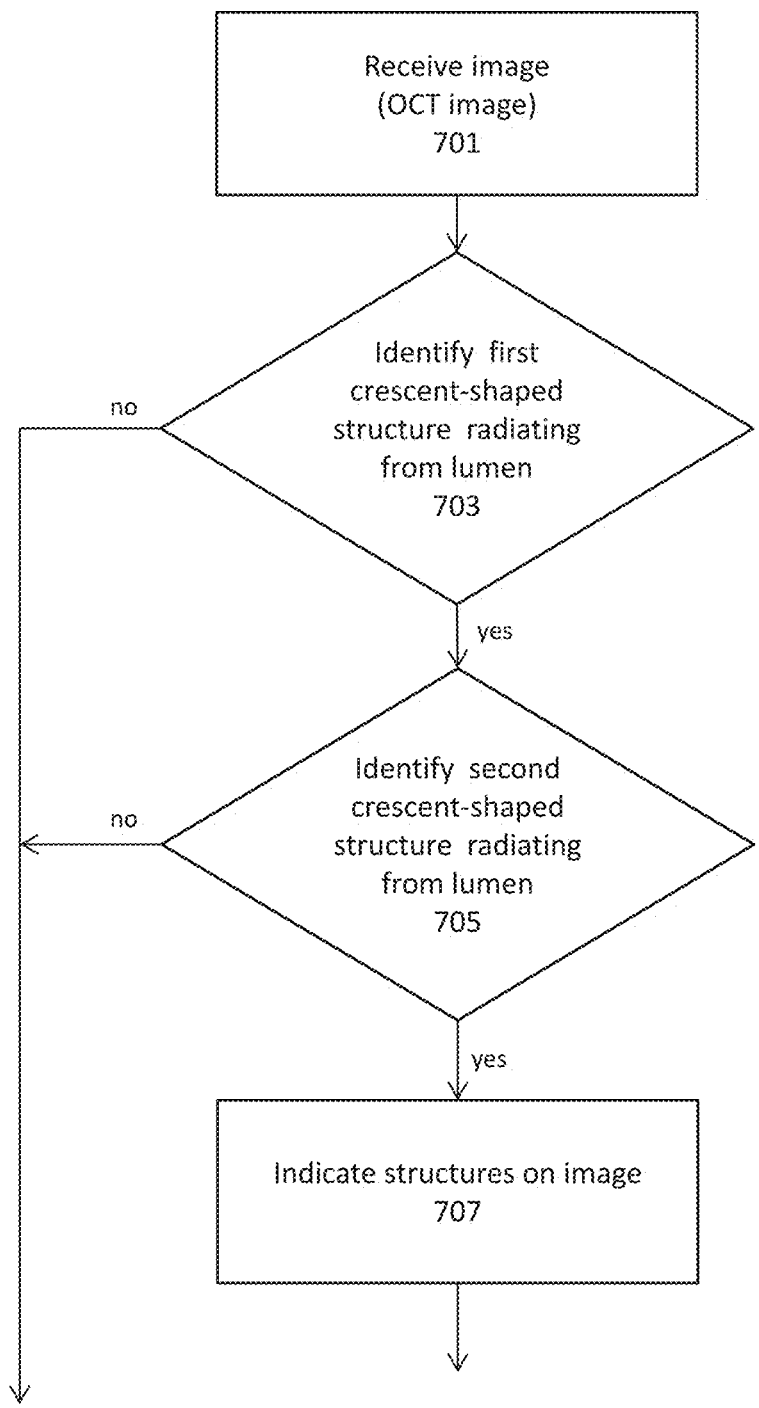
FIG. 7 illustrates one method of detecting crescent-shaped structures indicative of the boundaries of an atheroma as described herein.

FIG. 7 shows a schematic of one variation of a method of implementing an automatic detection of the crescent-shaped structures as discussed above. At step 701, an image, such as an OCT image, from within an anatomical lumen is obtained. At step 703, it can be determined whether there is a crescent-shaped structure radiating from the lumen in the image. If so, then it can be determined at step 705 whether there is a second crescent-shaped structure radiating from the lumen in the image. If so, then, at step 707, the first and second crescent-shaped structures can be used to identify anatomical structures within the lumen, such as a plaque mass and/or healthy tissue within the lumen.

Devices or systems, including atherectomy devices and/or systems, can be designed to take advantage of the morphology resulting from the crossing of the lesion and the previously unsuspected ability to reliably determine atheroma using these newly-recognized morphological markers. For example, a device may include a pre-shaped tip region that slides easily along/between the crescent shaped morphology. Thus, a therapeutic tool may take a shape that fits into the form factor provided by this morphology, facilitating advancement through a lesion, treatment of a plaque mass, and/or delivery of a therapeutic agent (e.g., pharmaceutical).

Thus, a device can utilize the shape that is formed at the boundary between the healthy vessel and the disease when the open lumen is distended by a dissection device. The device can utilize a form factor which matches that of the dissection that is observed at the interface between the disease and the healthy vessel. The profile of the tip of the device is formed into the crescent shape described above.

Figure 4:
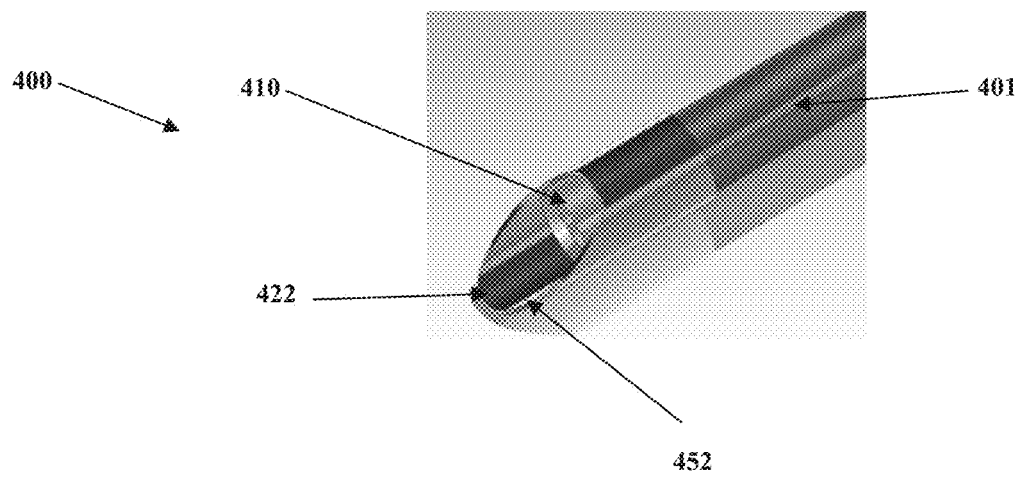
FIG. 4 illustrates one variation of an atherectomy device adapted as described herein.

For example, referring to FIG. 4, in one variation, the distal end of an atherectomy device 400 having a rotating cutter may be adapted to take advantage of the characteristic morphology of the vessel. As shown in FIG. 4, the atherectomy device can include an elongate catheter body 401 and a rotatable cutter 410 near the distal end of the catheter body 401. The elongate body can end in a beveled tip 422 (i.e. with a troweled or tongue-shaped opening) that extends distally past the rotatable cutter 410 on one side of the cutter 410 and proximal of the rotatable cutter 410 on the other side of the cutter 410. The troweled or tongue-shaped tip 422 is thus configured to protect a portion of the rotatable cutter 410 while the exposed portion of the cutter 410 is configured to be placed in the cleft of the crescent. The troweled or tongue-shaped tip 422 has an outer curved surface configured to slide along the healthy tissue of the vessel wall and a scooped inner edge 452 configured to at least partially plane along the lesion. Thus, referring to FIGS. 1-3, the outer curved surface is configured to be placed against the rounded portion 108 and the proximal end of the scooped inner edge 452 is configured to plane between the cat ears 101*a*, 101*b*. Such a configuration would thus place the cutter 410 against the substantially linear portion 109.

In one embodiment, the cutter 410 can be actuated by a hollow drive cable which also acts to capture and store the material that is excised from the interior of the vessel. The drive cable can reside in the lumen of the catheter body. Further, in one embodiment, an optical fiber can run through the drive cable. The distal end of the optical fiber can be mounted on the cutter. The optical fiber can thus run from the cutter to the proximal connector of the device. The proximal connector provides a way to both optically and mechanically couple the fiber and drive cable to the system driving the device. The optical fiber can provide a way to generate an image of the cross-section of the vessel via OCT.

The device 400 can be easily redirected based on features apparent in the OCT image, such as this crescent wing morphology, by promoting a blunt dissection along which the tip 422 of the device 400 will track. The orientation of the device can be adjusted via visual cues generated by the OCT, such as the crescent wings. The final orientation of the device can be defined by the conformance of the shape of the tip 422 of the device 400 with the dissection plane, as described above. Advancing the device 400 pushes the cutter 410 into the linear section visible in the OCT image that is indicative of diseased tissue. In doing so, the disease region may be excised and forced into the hollow center of the drive cable. Further advancing of the device 400 pushes more disease into the cutter 410. Continuing the distal movement of the device to the distal point of the stenosis creates a patent lumen facilitating blood flow and the passage of a wire or other adjunct device past the disease. Removal of the drive cable/cutter assembly from the center of the device during the procedure would facilitate using the device sheath as an exchange or delivery catheter.

The device described herein has several advantages. For example, the device facilitates atherectomy in the coronary vasculature via image-guided cutting. Moreover, it offers a safe way to perform the procedure by orienting the device such that the tip 422 protects the healthy vessel wall from damage by the cutter.

In addition to a device having a pre-shaped tip configured to conform to the crescent-shaped tissue morphology described above, in some embodiments a device can be configured to self-orient through the vessel. In other words, the outer curved surface could automatically align with the healthy, stretched outer tissue layers (e.g., adventitia) while the beveled edge and thus the cutter could automatically align with the occlusion. In some embodiments, therefore, the device may not require an imaging sensor.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. A system comprising:
   an elongate imaging catheter body comprising a sensor;
   a controller; and
   a non-transitory computer-readable medium including contents that are configured to cause the controller to perform a method comprising:
   obtaining, from the sensor on the elongate imaging catheter body, an image from within a blood vessel; and
   automatically detecting, labeling, and/or highlighting one or more crescent-shaped morphological structures in the image.

2. The system of claim 1, wherein the method performed by the controller further comprises automatically detecting a location of an atheroma based on the detected one or more crescent-shaped morphological structures.

3. The system of claim 1, wherein the method performed by the controller further comprises determining a direction in which the one or more crescent-shaped morphological structures point.

4. The system of claim 1, wherein the method performed by the controller further comprises determining a direction in which one or more of the one or more crescent-shaped morphological structures point and determining a location of an atheroma based on the direction.

5. The system of claim 1, wherein the method performed by the controller further comprises detecting a location of healthy tissue based on the detected one or more crescent-shaped morphological structures.

6. The system of claim 1, wherein the method performed by the controller further comprises displaying the detected one or more crescent-shaped morphological structures as real-time markers.

7. The system of claim 1, wherein the method performed by the controller further comprises, based upon images showing a characteristic one or more crescent-shaped morphology, aligning or steering the elongate imaging catheter body through the blood vessel.

8. The system of claim 1, wherein the elongate imaging catheter further comprises one or more reference markers, wherein the one or more reference markers are configured to produce corresponding reference regions in the image.

9. The system of claim 1, wherein the sensor comprises an optical coherence tomography (OCT) sensor on the elongate imaging catheter body.

10. The system of claim 1, further comprising a rotatable cylindrical cutter at or near a distal end of the elongate imaging catheter body.

11. A system comprising:
an elongate imaging catheter body comprising a sensor;
a cutter on the elongate imaging catheter body at or near a distal end of the elongate imaging catheter body; and
a controller comprising a non-transitory computer-readable medium including contents that are configured to cause the controller to perform a method comprising:
obtaining, from the sensor on the elongate imaging catheter body, an image from within a blood vessel;
automatically detecting, labeling, and/or highlighting one or more crescent-shaped morphological structures in the image; and
indicating a location of an atheroma based on the detected one or more crescent-shaped morphological structures.

12. The system of claim 11, wherein the method performed by the controller further comprises determining a direction in which the one or more crescent-shaped morphological structures point and determining the location of the atheroma based on the direction.

13. The system of claim 11, wherein the method performed by the controller further comprises detecting a location of healthy tissue based on detected one or more crescent-shaped morphological structures.

14. The system of claim 11, wherein the method performed by the controller further comprises displaying detected one or more crescent-shaped morphological structures as real-time markers on the image.

15. The system of claim 11, wherein the method performed by the controller further comprises, based upon images showing a characteristic one or more crescent-shaped morphology, aligning or steering the elongate imaging catheter body through the blood vessel.

16. The system of claim 11, further comprising one or more reference markers on the elongate imaging catheter body, wherein the one or more reference markers are configured to produce corresponding reference regions in the image.

17. The system of claim 11, wherein the sensor comprises an optical coherence tomography (OCT) sensor on the elongate imaging catheter body.

18. A method of identifying an atheroma within a blood vessel, the method comprising:
inserting a device into the blood vessel;
imaging the blood vessel with a sensor of the device to create an image;
identifying a location and orientation of a plurality of pointed crescent-shaped structures extending radially from a semi-circular or "D" shaped central portion in the image, wherein a controller automatically identifies the pointed crescent-shaped structures; and
determining a position of an atheroma within the blood vessel relative to the device based upon the identified location and orientation of the pointed crescent-shaped structures in the image.

19. The method of claim 18, wherein the semi-circular or "D" shaped central portion comprises a rounded portion and a linear portion, each pointed crescent-shaped structure extending from a junction of the rounded portion and the linear portion.

20. The method of claim 18, further comprising, with the controller, automatically orienting or steering the device through the blood vessel based upon a characteristic crescent-shaped morphology.

* * * * *